United States Patent [19]

Sunaga

[11] 4,425,025
[45] Jan. 10, 1984

[54] OPTICAL SYSTEM FOR ENDOSCOPES

[75] Inventor: Yasumasa Sunaga, Iwatsuki, Japan

[73] Assignee: Fuji Photo Optical Co., Ltd., Ohmiya, Japan

[21] Appl. No.: 217,556

[22] Filed: Dec. 17, 1980

[30] Foreign Application Priority Data

Dec. 26, 1979 [JP] Japan .................... 54-169587

[51] Int. Cl.³ .............................. G02B 5/17
[52] U.S. Cl. .................. 350/96.26; 350/410; 350/427
[58] Field of Search .......... 350/96.25, 96.26, 410, 350/423, 427

[56] References Cited

U.S. PATENT DOCUMENTS

| 2,987,960 | 6/1961 | Sheldon | 350/96.25 X |
|---|---|---|---|
| 3,576,358 | 4/1971 | Hayamizu et al. | 350/96.25 X |
| 3,637,282 | 1/1972 | Hayamizu et al. | 350/96.25 X |
| 4,101,196 | 7/1978 | Imai | 350/96.25 X |
| 4,269,485 | 5/1981 | Yamashita et al. | 350/96.26 X |
| 4,285,578 | 8/1981 | Yamashita et al. | 350/410 |
| 4,312,572 | 1/1982 | Yamashita et al. | 350/423 |

FOREIGN PATENT DOCUMENTS 2544519  4/1976  Fed. Rep. of Germany ... 350/96.26

Primary Examiner—John D. Lee
Assistant Examiner—Frank Gonzalez

[57] ABSTRACT

A wide angle objective is located at the entrance face of a flexible image guide tube of an endoscope and a variable focal length eyepiece lens system is located at the exit face of the tube. The variable focal length eyepiece lens system includes an axially movable lens group which increases the magnification of the endoscope from the normal 20 times to about 40 times, in effect, increasing the magnification 20 times over the magnification potential of current endoscopes.

2 Claims, 2 Drawing Figures

OPTICAL SYSTEM FOR ENDOSCOPES

BACKGROUND OF THE INVENTION

1. Field of the Invention

This invention relates to an optical system for an endoscope having a wide angle view, and more particularly to a wide angle optical system for an endoscope which is capable of varying its focal length for varying the magnification of the image viewed.

2. Description of the Prior Art

Recently, there has been a great demand for an endoscope for viewing the interior of a human body which has a large angle of view and has a thin flexible tube to be inserted into the body. A thinner tube is highly desirable since it decreases the possibility of pain when inserted into the body.

However, in order to make the angle of view wide and the thickness of the flexible tube or the optical fiber bundle of the endoscope small, the size of the image viewed would normally be greatly reduced. A reduced image would cause the eyes of the operator to become tired and lower the diagnostic efficiency and accuracy of the endoscope. Further, the smaller the image becomes, the more difficult become the operation of forceps and the cannulation of the duodenum. It becomes very difficult for doctors who are accustomed to use forceps with a conventional angle of view and image size to use them with the large angle of view.

For the above reasons, it is desirable to have means to enlarge the angle of view of the eyepiece when desired. There are three methods for enlarging the angle of view or changing the magnification of the eyepiece of an endoscope, as follows.

The first method is to mount an adaptor consisting of an optical system having the proper magnification on the eyepiece to change the effective magnification of the eyepiece. The second method is to incorporate a magnification changing lens into the lens system of the eyepiece. The third method is to make a part or the whole of the eyepiece movable to change the magnification.

The first method, however, is disadvantageous in that it requires an additional operation to mount the adapter on or remove the same from the eyepiece. The second method is disadvantageous in that inevitably the size and weight of the eyepiece portion of the endoscope becomes larger. Further, the operation of this endoscope becomes more complex and the brightness of the images viewed through the lens markedly changes when a magnification changing lens is incorporated.

The third method, however, is advantageous in that the magnification can easily be changed with a simple operation, not requiring the troublesome operations of mounting and removing the lens. Further, the lens group can be made so that it has a compact size and light weight. In addition, diopter adjustments can easily be made by simply moving a part of the eyepiece lens system. Furthermore, while the external shape of the eyepiece portion may not be changed in the second method, any accessory, like a camera or a visualizing scope, can easily be mounted on the eyepiece in this third method.

SUMMARY OF THE INVENTION

It is, therefore, the primary object of the present invention to provide a wide angle optical system for an endoscope capable of varying its focal length according to the third method described above.

A more specific object of the present invention is to provide a focal length variable eyepiece lens system for an endoscope, which is able to vary its magnification to as large as 40 times, compared to the conventionally popular magnification of 18-20 times.

The above objects of the present invention can be accomplished by providing a wide angle objective at the top of the endoscope for viewing the interior of a human body or the like, and providing a focal length variable eyepiece. Between the objective and the eyepiece there is an image guide, a flexible optical fiber bundle, for transmitting an image from one end to the other. The variable focal length lens eyepiece can be made by making a part, or the whole of the eyepiece lens system, like a conventional variable focal length lens system or a zoom lens system. Further, by making at least a part of the eyepiece lens system movable, diopter adjustments can easily be made.

In accordance with the present invention in which the objective at the top of the endoscope has a wide angle view and the eyepiece has a variable focal length, it is possible to view the interior of the stomach or duodenum with a wide angle view and increase the magnification so as to see a part of the image with the desired magnification with a very simple operation. Therefore, diagnoses and medical treatments are made more easily with the use of the endoscope. Further, forceps can be used more accurately and more easily by making the angle of view the same as the conventional view.

DESCRIPTION OF THE PREFERRED EMBODIMENTS

Now the present invention will be described in detail referring to the accompanying drawings.

Figure 1:
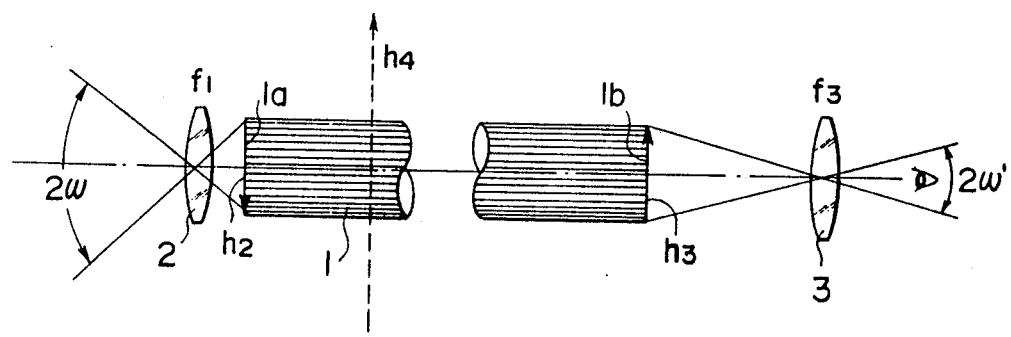
FIG. 1 is a schematic view showing the optical system of an endoscope.

FIG. 1 shows the whole optical system of an endoscope, embodying the present invention. The endoscope is mainly composed of an image-guiding flexible tube 1 having an entrance face 1a for receiving light from the interior to be observed or photographed and an exit face 1b from which the image of the interior can be viewed. At the entrance face 1a a wide angle objective 2 is provided for focusing an image of the object or the interior to be observed or photographed on the entrance face 1a with a wide angle of view. At the exit face 1b a variable focal length eyepiece lens system 3 is provided for viewing the image at the desired magnification. In more detail, on the entrance face 1a of the image guiding flexible tube or optical fiber bundle 1 is focused an image $h_2$ by the objective 2, and on the exit face 1b of the image guiding flexible tube 1 appears an image $h_3$. By an eyepiece 3 having a focal length of $f_3$ a virtual image $h_4$ of the image $h_3$ is viewed in enlarged scale.

In an endoscope employing the conventional optical system, the angle of view $2w$ of the objective 2 is about 60° to 70°, and the magnification of the eyepiece is normally 18 to 22 times and the effective angle of view $2w'$ is about 8° to 12°. Under the circumstances, when the angle of view of the objective 2 is enlarged to 100° or more (2w≧100°), the angle of view is enlarged to about 1.5 times to 2 times as large as the conventional one. However, the size of the image $h_2$ focused on the entrance face $1a$ of the image guiding tube cannot be made so large due to restriction as the outer diameter of the endoscope. Therefore, the magnification of the image $h_2$ cannot be enlarged over 1.2 times as large as the conventional one. Consequently, with said effective angle of view of the eyepiece, the size of the image appearing on the exit face $1b$ of the image guiding tube 1 becomes small and is viewed in reduced scale. This is disadvantageous in that the image is hard to see for the observer who is accustomed to see the conventional size image. In order to solve this problem, it is possible to increase the magnification of the eyepiece which results in enlargement of the size of the virtual image $h_4$. However, if the magnification of the eyepiece is enlarged, the appearance of the exit face $1b$ of the optical fiber bundle 1 is also enlarged and the image quality of the observed image is deteriorated. Thus, it is undesirable to enlarge the image magnification over a certain value. On the other hand, when the magnification of the eyepiece 3 is too much increased in this invention, the eyepiece lens system becomes too large and heavy. Therefore, from this viewpoint also, it is undesirable to increase the magnification over a certain value. In view of these considerations, the magnification of the eyepiece or the focal length varying ratio is preferably about twice.

Further, it will be noted that the variable focal length eyepiece lens system 2 is advantageous in comparison with an eyepiece lens system having a discontinuously changeable focal length, in that the size of the image can easily and instantly be varied to any desired value.

Further, it will be understood that there may be used a mask in the optical path of the endoscope, for instance between the exit face $1b$ and the eyepiece 3, when it is not necessary to see the whole field of view of the image or it is desired to cut a part of the field of view.

Figure 2:
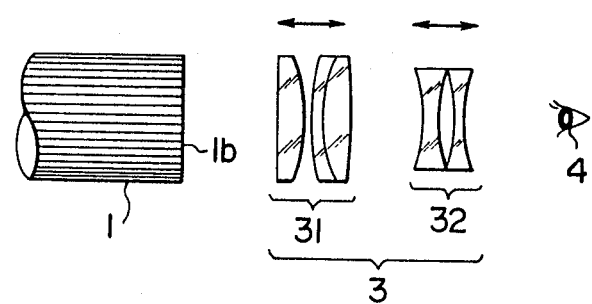
FIG. 2 is a schematic view showing an example of the eyepiece lens system employed in the present invention.

FIG. 2 shows an example of the variable focal length eyepiece lens system 3, which is composed of a positive lens group 31 located close to the exit face $1b$ of the image-guiding flexible tube 1 and a negative lens group 32 located at a remote distance from the exit face $1b$. The two lens groups 31 and 32 of the variable focal length eyepiece lens system 3 are both axially movable to vary the effective or composite focal length by varying the distance of the positive lens group 31 from the exit face $1b$ and varying the distance between the two lens groups 31 and 32. By properly moving these lens groups 31 and 32 according to a predetermined relationship with respect to the exit face, it is possible to vary the focal length without affecting the focus of the image viewed by an eye 4 of the observer. The magnification of the eyepiece lens system 3 is thus variable between 20 times to 40 times. As a result, for instance the angle of view of the endoscope is variable between a wide angle of view of about 100° and a conventional angle of view of 60°.

I claim:

1. An optical system for an endoscope, comprising: a flexible image guide optical fiber bundle having an entrance face at one end thereof and an exit face at the other end thereof, a wide angle objective adjacent said entrance face for focusing an image to be observed on said entrance face, a variable focal length eyepiece lens system located adjacent said exit face for viewing an image appearing on said exit face, said variable focal length eyepiece lens system comprising a positive lens group, and a negative lens group, said positive lens group being axially movable to vary the distance thereof from said exit face of said optical fiber bundle, and said negative lens group being axially movable to vary the distance between the same and the positive lens group.

2. An optical system for an endoscope according to claim 1, wherein said negative movable lens group serves for diopter adjustment.

* * * * *